(12) United States Patent
Tanriover et al.

(10) Patent No.: US 10,299,716 B2
(45) Date of Patent: May 28, 2019

(54) SIDE FACE IMAGE-BASED MENTAL STATE DETERMINATION

(71) Applicant: Intel Corporation, Santa Clara, CA (US)

(72) Inventors: Cagri Tanriover, Istanbul (TR); Sinem Aslan, Istanbul (TR); Nese Alyuz Civitci, Istanbul (TR); Ece Oktay, Istanbul (TR); Eda Okur, Istanbul (TR); Asli Arslan Esme, Istanbul (TR)

(73) Assignee: Intel Corporation, Santa Clara, CA (US)

( * ) Notice: Subject to any disclaimer, the term of this patent is extended or adjusted under 35 U.S.C. 154(b) by 68 days.

(21) Appl. No.: 15/389,051

(22) Filed: Dec. 22, 2016

(65) Prior Publication Data

US 2017/0188928 A1     Jul. 6, 2017

(51) Int. Cl.
    *A61B 5/01*         (2006.01)
    *A61B 5/16*         (2006.01)
    *G06F 1/16*         (2006.01)
    *A61B 5/0402*     (2006.01)
    *A61B 5/0476*     (2006.01)
    (Continued)

(52) U.S. Cl.
CPC .......... *A61B 5/165* (2013.01); *A61B 5/14551* (2013.01); *G06F 1/163* (2013.01); *H04N 7/183* (2013.01); *A61B 5/01* (2013.01); *A61B 5/021* (2013.01); *A61B 5/02416* (2013.01); *A61B 5/0402* (2013.01); *A61B 5/0476* (2013.01);
(Continued)

(58) Field of Classification Search
CPC ........... A61B 5/165; A61B 5/021; A61B 5/02; A61B 5/04; G06K 9/00302; G06K 9/00221; G06K 9/00315; G06K 9/00335; G06F 1/163; G06F 1/1686
See application file for complete search history.

(56) References Cited

U.S. PATENT DOCUMENTS 5,859,921 A * 1/1999 Suzuki ............... G06K 9/00268
                                                       382/118
6,920,236 B2 * 7/2005 Prokoski ............ G06K 9/00221
                                                        356/71

(Continued)

OTHER PUBLICATIONS

Chang, "A Subject-Dependent Facial Expression Recognition System", Chapter 4 of Emotion Recognition: A Pattern Analysis Approach, Wiley 2014.*

(Continued)

*Primary Examiner* — Jessica M Prince
*Assistant Examiner* — Michael Robert Cammarata
(74) *Attorney, Agent, or Firm* — Jordan IP Law, LLC (57) ABSTRACT

Apparatus, systems, and/or methods may provide a mental state determination. For example, a data collector may collect image data for a side of a face of a user from an image capture device on the user (e.g., a wearable device). The image data may include two or more perspectives of a feature on the side of the face of the user. In addition, a state determiner may determine a mental state of the user based on the image data. In one example, fields of view may be combined to determine a total region and/or a total overlap region. Changing the position that one or more image capture devices point may modulate the total region and/or the total overlap region. In addition, one or more sensors may be utilized to further improve mental data determinations.

22 Claims, 3 Drawing Sheets

(51) Int. Cl.
  *A61B 5/1171* (2016.01)
  *H04N 7/18* (2006.01)
  *A61B 5/1455* (2006.01)
  *A61B 5/08* (2006.01)
  *A61B 5/021* (2006.01)
  *A61B 5/024* (2006.01)
  *A61B 5/145* (2006.01)

(52) U.S. Cl.
  CPC .......... *A61B 5/0816* (2013.01); *A61B 5/1176* (2013.01); *A61B 5/145* (2013.01)

(56) References Cited

U.S. PATENT DOCUMENTS

| | | | |
|---|---|---|---|
| 9,934,425 B2* | 4/2018 | el Kaliouby | G06K 9/00302 |
| 10,165,949 B2* | 1/2019 | Tzvieli | A61B 5/015 |
| 2003/0058111 A1* | 3/2003 | Lee | G06K 9/00342 |
| | | | 340/573.1 |
| 2003/0164874 A1* | 9/2003 | Sawada | G06F 1/1616 |
| | | | 348/36 |
| 2004/0193068 A1* | 9/2004 | Burton | A61B 5/0476 |
| | | | 600/544 |
| 2010/0086215 A1* | 4/2010 | Bartlett | G06K 9/00335 |
| | | | 382/197 |
| 2010/0123776 A1* | 5/2010 | Wydeven | H04N 7/183 |
| | | | 348/77 |
| 2011/0301433 A1* | 12/2011 | Sadowsky | A61B 5/165 |
| | | | 600/300 |
| 2016/0287166 A1* | 10/2016 | Tran | H04B 1/3827 |
| 2017/0117005 A1* | 4/2017 | Jerauld | G10L 25/63 |
| 2018/0077356 A1* | 3/2018 | Zilberman | H04N 5/23296 |
| 2018/0103889 A1* | 4/2018 | Tzvieli | A61B 5/411 |
| 2018/0103903 A1* | 4/2018 | Tzvieli | A61B 5/6803 |

OTHER PUBLICATIONS

Zheng, "Emotion Recognition From Non-Frontal Facial Images", Chapter 8 of Emotion Recognition: A Pattern Analysis Approach, Wiley 2014.*

Manuel Marques, 3D face recognition from multiple images: a shape-from-motion approach, Institute for Systems and Robotics (IRS)—Instituto Superior Técnico(IST), Av. Rovisco Pais—1049-001 Lisboa Portugal (2008) (Year: 2008).*

The POSTECH Face Database (PF07) and Performance Evaluation 2008 8th IEEE International Conference on Automatic Face & Gesture Recognition (Year: 2008).*

* cited by examiner

SIDE FACE IMAGE-BASED MENTAL STATE DETERMINATION

CROSS-REFERENCE RELATED APPLICATIONS

The present application claims benefit of priority to International Patent Application No. PCT/US2015/000330, filed Dec. 24, 2015.

TECHNICAL FIELD

Embodiments generally relate to mental state determination. More particularly, embodiments relate to determining a mental state of a user based on image data from a wearable image capture device on the user.

BACKGROUND

Wearable devices to calculate a mental state may include a camera that points away from a wearer and towards another person being observed. In addition, wearable devices may be in a field of view or sight line of the wearer. Additionally, wearable devices may not move to capture data. Moreover, only a single perspective may be provided. Such wearable devices, therefore, may increase relative inconvenience to a wearer, reduce relative reliability to calculate a mental state, etc. Thus, there is considerable room for improvement to determine a mental state.

BRIEF DESCRIPTION OF THE DRAWINGS

The various advantages of embodiments will become apparent to one skilled in the art by reading the following specification and appended claims, and by referencing the following drawings, in which:

DESCRIPTION OF EMBODIMENTS

FIGS. 1A-1D illustrate an example of an apparatus 10 to determine (e.g., infer, predict, calculate, etc.) a mental state of a user 12 according to an embodiment. The mental state may include an emotional state, a cognitive state, and/or a mental response unconsciously triggered by the nervous system. Thus, the apparatus 10 may determine frustration, confusion, disappointment, hesitation, cognitive overload, focusing, engagement, attention, boredom, exploration, confidence, trust, delight, disgust, skepticism, doubt, satisfaction, excitement, laughter, calmness, stress, curiosity, paranoia, approval, understanding, sympathy, empathy, indifference, etc.

In the illustrated example, image capture devices 14 (14a-14c) may capture image data for a side 16 of a face 18. The image capture devices 14 may include, for example, a video camera, a still camera, a thermal imager, a charged coupled device (CCD), a three-dimensional (3D) camera, a two-dimensional (2D) camera, a depth camera, and so on. In addition, the image capture devices 14 may move independently of each other. For example, the image capture devices 14 may be disposed on an assembly (e.g., a head mount assembly, a shoulder mount assembly, a battery operated head-worn wearable device, etc.) and independently move outside of a field of view or a sight line of the user 12 to capture image data.

While the illustrated image capture devices 14 are substantially vertically aligned with one another, the position of the image capture devices 14 may be changed by utilizing multiple assemblies, by utilizing flexible members (e.g., arms, bands, etc.), and so on. The image capture devices 14 may also be slidably coupled (e.g., via a slide coupler on the assembly, etc.) with the user 12 to move along an axis in any direction (e.g., along a 2D Cartesian plane, etc.). In addition, the image capture devices 14 may be rotatably coupled (e.g., via a socket-joint coupler on the assembly, etc.) with the user 12 to rotate about corresponding central axes with any rotational degree of freedom (e.g., a 360-degree rotational freedom, etc.).

In the illustrated example, the image capture devices 14 are rotatably coupled with the user 12 via an ear mount assembly 20 to capture image data independently of each other and to provide various perspectives of a feature. For example, the image capture devices 14 may each rotatably pan across the side 16 (e.g., right side) of the face 18, concurrently or sequentially, when capturing image data. In another example, only one image capture device, such as the image capture device 14b, may be utilized to pan across the side 16 of the face 18 and capture image. In a further example, the image capture devices 14 may each rotatably move about corresponding central axes to be positioned for concurrent capture of image data when at rest. The number, location, movement, synchronization, resolution, etc., of the image capture devices 14 may be predetermined or specified by the user 12.

Notably, the feature may be any area on the face 18 within a field of view of the image capture devices 14. The feature may also include a landmark feature such as, for example, a jaw, a cheek (e.g., a cheekbone, a jowl, etc.) a dimple, an eye socket, an eyebrow, a temple, a hairline, a crease or furrow (e.g., a forehead furrow, eye crease, etc.), and so on. In addition, the feature may include a partial feature and/or a whole feature. A partial feature may include a feature (e.g., an area, a forehead furrow, etc.) extending over more than one side of the face 18 whose part on the side 16 is captured by the image capture devices 14, individually or collectively. A partial feature may also include a feature (e.g., an area, eyebrow, etc.) entirely on the side 16 whose part (e.g., eyebrow start, etc.) is captured by the image capture devices 14, individually or collectively. A whole feature may include a feature (e.g., an area, dimple, etc.) entirely on the side 16 that is captured in its entirety by the image capture devices 14, individually or collectively.

Figure 1A:
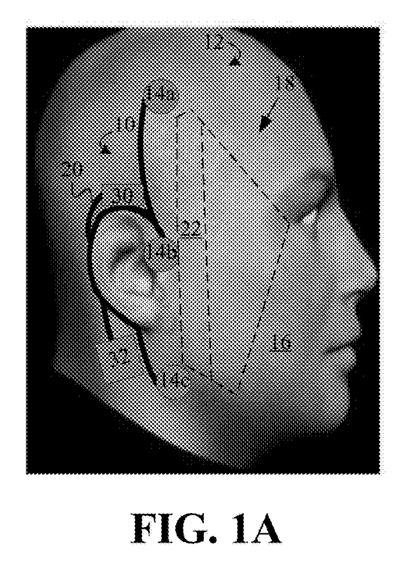
FIGS. 1A-1D are examples of an apparatus to determine a mental state according to an embodiment.

As shown in FIG. 1A, the feature may include an area 22 that may not be observable when facing the user 12. Unconventional locations and/or angles of the image capture devices 14 allow information rich image data, including the area 22, to be captured that may conventionally be unobservable by a person and/or a camera facing the user 12. Image data for multiple conventionally unobservable areas may also be captured by image capture devices disposed on a right side and a left side of the face 18. Unconventional locations and/or angles of the image capture devices may also provide more accurate and/or reliable predictions by minimizing distraction, device induced emotion, etc. In the illustrated example, image data for a plurality of features (e.g., a part of a jaw, cheek, eye socket, etc.) may also be captured.

Figure 1B:
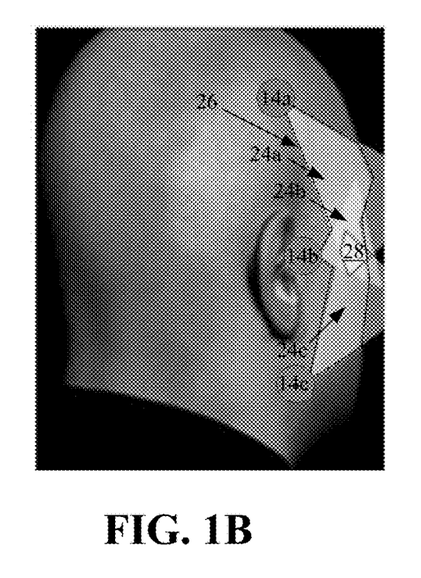

As shown in FIG. 1B, fields of view 24 (24a-24c) (shown as triangles for illustration) of the image capture devices 14 may provide multiple perspectives of a feature, of the face 18, and so on. In the illustrated example, the image capture device 14a is disposed at a first angle relative to the face 18 (e.g., downward angle relative the facial transverse plane, etc.) and includes a field of view 24a that provides a first perspective of the feature. In addition, the image capture device 14b is disposed at a second angle relative to the face 18 (e.g., perpendicular to the facial midsagittal plane, etc.) and includes a field of view 24b that provides a second perspective of the feature. Moreover, the image capture device 14c is disposed at a third angle relative to the face 18 (e.g., upward angle relative to the facial transverse plane, etc.) and includes a field of view 24c that provides a third perspective of the feature.

In another example where the image capture devices 14a, 14c are omitted, the field of view 24b may also provide at least part of the perspectives of the feature provided by the fields of view 24a, 24c when the image capture device 14b pans across the face 18. In this case, the field of view 24b may also provide multiple perspectives of the feature relative to an initial perspective that the field of view 24b initially provides. Thus, for example, the image capture devices 14 may capture image data including multiple perspectives of the area 22, a part of the eye socket, a part of the temple (FIG. 1A), discussed above, and so on.

The fields of view 24 may be combined to define a total region 26. The total region 26 may include a relatively large section on the side 16 that is captured by the image capture devices 14, concurrently or sequentially. The total region 26 may also include an overall section on the side 16 that provides an overall facial state captured by the image capture devices 14, concurrently or sequentially. The total region 26 may provide a larger quantity of features that may increase accuracy and/or reliability of predictions derived for a particular section of the face 18. In addition, the fields of view 24 may be combined to define a total overlap region 28 that is captured by the image capture devices 14, concurrently or sequentially. The total overlap region 28 may provide focused features that may also increase accuracy and/or reliability of predictions derived for a particular section of the face 18.

In the illustrated example, the perimeter of the total region 26 may be determined based on a boundary between the fields of view 24 and the face 18. In addition, the perimeter of the total overlap region 28 may be determined based on the area of overlap among the fields of view 24. Notably, an amount of overlap of the fields of view 24 may be modulated (e.g., moved, resized, etc.) to define a dimension and/or a position of the total region 26 and/or the total overlap region 28. The amount of overlap of the fields of view 24 may be scaled to the size and location of a feature.

Figure 1C:
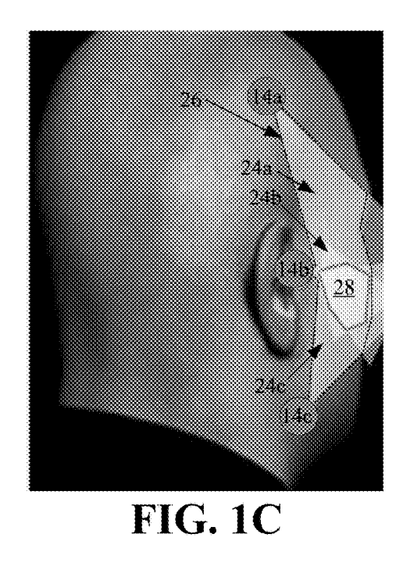
Figure 1D:
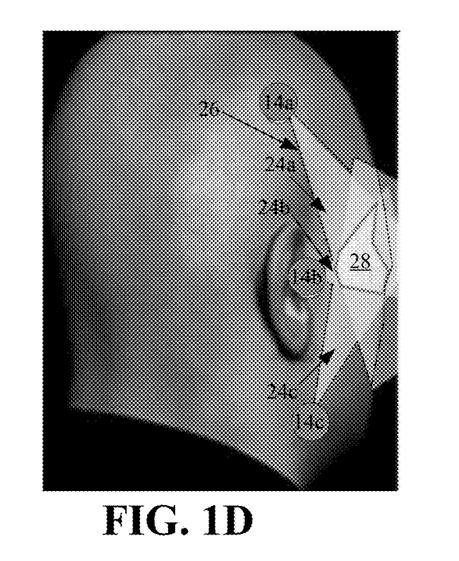

As shown in FIGS. 1C and 1D, the total region 26 and the total overlap region 28 may be moved and resized by changing a direction that the image capture devices 14 point. In this regard, an ability to define at least the total overlap region 28 may improve visual input information accuracy and/or reliability since an amount of state information (e.g., emotion data, etc.) may vary over time. For example, a jowl and/or a cheekbone may rise when the user 12 is happy and fall when the user 12 is unhappy. In another example, an eye crease may appear when the user 12 is focused and disappear when the user 12 is unfocused.

Moving or resizing at least the total overlap region 28 to include (or focus on) a section of the face 18 (e.g., the jowl) may speed up evaluations for mental state recognition to achieve real-time operation. For example, the acquisition of metrics (e.g., captured features, identified features, retrieved characteristic features, retrieved user specific features, etc.) may be relatively faster. In addition, moving or resizing the total overlap region 28 to include (or focus on) a section of the face 18 may provide an ability to track movement at a finer granularity, features on-the-fly, and so on. Moving or resizing the total region 26 may provide a larger quantity of metrics that may be used to elucidate or corroborate accuracy and/or reliability of predicted states. Also, the speed of evaluations and/or the confidence of predicted states may further benefit from a plurality of perspectives, e.g., captured concurrently, sequentially in a relatively narrow time window (e.g., as a camera pans, etc.), etc.

Positions and/or angles of the image capture devices 14 may be calibrated for the user 12 (e.g., user specific angles, etc.). Calibration may occur, for example, at boot up, in response to a change in power state, and so on. The calibration may maximize an effectiveness of image data in the total region 26 and/or in the total overlap region 28. In addition, the calibration may minimize (e.g., eliminate, etc.) a need for separate registration of each captured image. The positions and/or the angles may also be set and/or changed at any time to modulate the total region 26 and/or the total overlap region 28. The positions and/or the angles may vary based on a perspective preference (e.g., a number of perspectives, a direction of perspectives, etc.), a region preference (e.g., a dimension, a position, etc.), a feature preference (e.g., an area dimension, an area location, a specific feature, a number of features, etc.), an accuracy preference (e.g., statistically significant feature movements, corroboration, etc.), an efficiency preference (e.g., speed of evaluation, etc.), etc.

Thus, the image capture devices 14 may capture image data (e.g., video, snapshots, etc.) of various sections of the face 18 continuously, concurrently, and/or sequentially to provide an overall or collective evaluation of the feature (e.g., various perspectives of various features, which may include conventionally unobservable areas) via the total region 28. In addition, a granularity at which the image capture devices 14 capture image data may vary via the total overlap region 28, which may speed up evaluations and/or improve confidence of predicted states.

Referring back to FIG. 1A, the ear mount assembly 20 further includes a processor 30, which may implement and/or coordinate actions of any or all components of the ear mount assembly 20. For example, the processor 30 may adjust the image capture devices 14 (e.g., rotate to a position, pan, etc.). In addition, the processor may also provide image data capture parameters such as shutter, resolution, speed, synchronization, and so on. Moreover, the processor 30 may process the image data, and/or may forward the image data via a communications interface to be processed. The processor 30 may also receive data (e.g., guidance, etc.) via the communications interface to be used and/or output by the processor 30

Additionally, the processor 30 may determine the total region 26 and/or the total overlap region 28, identify and/or extract a feature (e.g., an area of interest, a feature of interest, etc.) in regions 26, 28, and evaluate the feature. In this regard, the processor 30 may recognize expressions, head gestures, smiles, brow furrows, lowered eyebrows, raised eyebrows, squints, attention, arousal, valence, leaning, etc., from the image data to determine the mental state of the user 12. The processor 30 may also determine physiological data from the image data such as relative temperature (e.g., sweat, etc.), pain (e.g., jaw clench, etc.), and so on.

The processor 30 may also retrieve characteristic mental state data including characteristic data for a mental state, user specific mental state data for a particular user, and so on. The processor may retrieve mental state data from an on-platform repository such as memory or storage, from an on-platform repository via the communications interface, and so on. In addition, the processor 30 may compare the image data with the characteristic mental state data and/or the user specific mental state data to determine the state of the user 12.

The processor 34 may further process sensor data from a sensor anywhere on the user 12. For example, a physiological sensor may collect physiological data such as electrodermal activity, skin temperature, accelerometer data, heart rate, blood pressure, electrocardiogram (ECG) data, electroencephalogram (EEG) data, brain wave data, and so on. As shown in FIG. 1A, the ear mount assembly 20 includes a physiological sensor 32, such as an electromyogram (EMG) sensor and/or a photoplethysmograph (PPG) sensor, that is positioned at an area with muscle mass, vasculature (e.g., veins, arteries, etc.), etc., to improve relative accuracy and/or reliability.

Generally, an EMG sensor may detect involuntary muscle movements that are indicators of stress, sadness, and nervousness, and so on. In addition, a PPG sensor may be used to measure signals such as heart rate, oxygen saturation, and breathing rate, which are indicators of sadness, nervousness, happiness, and so on. Thus, confidence of predicted states may increase when physiological data is evaluated together with image data to determine the state of the user 12. The physiological sensor 32 may be positioned, for example, on any area of the face 18 with muscle mass and/ or vasculature, any area of the neck of the user 12 with muscle mass and/or vasculature (e.g., surrounding the ear, etc.), and so on.

In addition, the processor 30 may provide the state of the user 12 to a state repository on-platform (e.g., storage, memory, etc.), off-platform (e.g., server, computing cloud server, memory, storage, etc.), and so on. The processor 30 may also provide the state of the user 12 to a function such as an application, a program, an operating system, and so on. Moreover, the processor 30 may provide the state of the user 12 to an entity, such as a rating entity, a social media entity, a news entity, an educational entity, an administrator, a third-party reseller, and so on.

Thus, ear mount assembly 20 may have communication functionality such as wireless communication functionality including, for example, cellular telephone (e.g., Wideband Code Division Multiple Access/W-CDMA (Universal Mobile Telecommunications System/UMTS), CDMA2000 (IS-856/IS-2000), etc.), WiFi (Wireless Fidelity, e.g., Institute of Electrical and Electronics Engineers/IEEE 802.11-2007, Wireless Local Area Network/LAN Medium Access Control (MAC) and Physical Layer (PHY) Specifications), 4G LTE (Fourth Generation Long Term Evolution), Bluetooth (e.g., Institute of Electrical and Electronics Engineers/IEEE 802.15.1-2005, Wireless Personal Area Networks), WiMax (e.g., IEEE 802.16-2004, LAN/MAN Broadband Wireless LANS), Global Positioning System (GPS), spread spectrum (e.g., 900 MHz), NFC (Near Field Communication, ECMA-340, ISO/IEC 18092), and other radio frequency (RF). In one example, the processor 30 may forward image data, sensor data, determined mental states, etc. to an off-platform repository, function, entity, device, and so on.

While examples have provided various components of the apparatus 10 for illustration purposes, it should be understood that one or more components of the apparatus 10 may reside in the same and/or different physical and/or virtual locations, may be combined, omitted, bypassed, re-arranged, and/or be utilized in any order.

Figure 2:
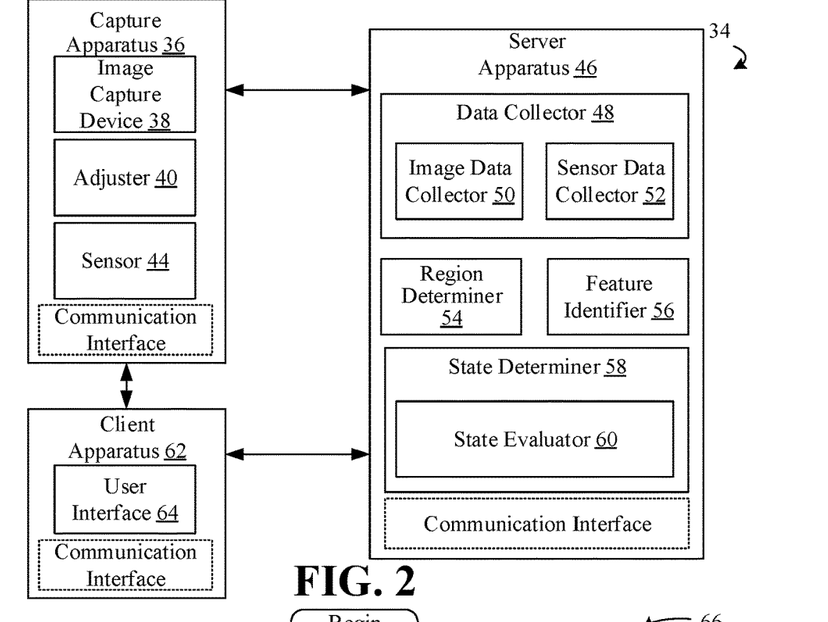
FIG. 2 is an example of a system to determine a mental state according to an embodiment.

Turning now to FIG. 2, a system 34 may include a capture apparatus 36 to capture data for a user, a server apparatus 46 to process the data, and a client apparatus 62 to render the data. In one example, image data may include a feature such as an area on a side of a face, a partial feature on the side of a face, a whole feature on the side of the face, a landmark feature on the side of the face, and so on. In addition, one or more image capture devices 38 may be disposed on opposing sides of the face (e.g., a predetermined number of cameras on each side of the face, etc.) to capture image data including a plurality of areas, a plurality of features, and so on.

The image capture devices 38 may be moveably coupled with the user to capture image data. In one example, a first perspective of a feature may be defined by a field of view of an image capture device 38 on the user at a first angle relative to the face, and a second perspective of the feature may be defined by the same field of view of the same image capture device 38 on the user at a second angle relative to the face. For example, the image capture device 38 may be moveably coupled with the user to pan across the side of the face of the user to capture the image data while panning.

In another example, a first perspective of a feature may be defined by a field of view of a first image capture device 38 on the user at a first angle relative to the face, and a second perspective of the feature may be defined by a field of view of a second image capture device 38 on the user at a second angle relative to the face. For example, two or more image capture devices 38 may be moveably coupled with the user to be positioned (e.g., at particular angles, etc.) to concurrently capture the image data when the image capture devices 38 are at rest (e.g., no longer rotating).

The capture apparatus 36 further includes an adjuster 40 to move the image capture devices 38 via an actuator and/or in response to guidance to a user (e.g., a wearer, etc.). The adjuster 40 may, for example, automatically calibrate an angle of the image capture devices 38 for the user relative to a plane of the face, relative to an area of the face, relative to a feature, relative to another image capture device on the user, and so on. Calibration may occur at boot time, in response to a change in power state (e.g., full power mode, etc.), and so on. The adjuster 40 may also adjust a position and/or an angle of the image capture devices 38 to modulate a total region and/or a total overlap region. In one example, a region preference may be used to set a total panning distance to define the total region. In another example, a feature preference may include a feature used to define the total overlap region.

The capture apparatus 36 further includes a sensor 44, which may capture sensor data (e.g., physiological data, etc.) of the user. The sensor 44 may include an EMG sensor, a PPG sensor, and so on. In addition, the capture apparatus 36 may include other components such as, for example, a communications interface to communicate data, a processor to process data, a repository to store data, a power supply to provide power to one or more components of the capture apparatus 36, and so on. For example, the capture apparatus 36 may provide image data and sensor data to the server apparatus 46 via respective communication interfaces.

The server apparatus 46 includes a data collector 48 to collect data captured by the capture apparatus 36. The data collector 48 includes an image data collector 50 to collect image data of the user and a sensor data collector 52 to collect sensor data of the user. In addition, the server apparatus 54 includes a region determiner 54 to determine a total region on the side of the face of the user. For example, two or more fields of view of two or more corresponding image capture devices 38 may be combined to define the total region. The region determiner 54 may also determine a total overlap region from the combination of the two or more fields of view of the two or more corresponding image capture devices 38.

The region determiner 54 may combine the image data (e.g., stitch still images, stitch video frames, combine depth data, etc.) from one or more image capture devices 38 to generate composite image data (e.g., a composite image, etc.) and determine a total region and/or a total overlap region from the composite image data. The region determiner 54 may also extract portions of the image data corresponding to the user's face before or after generating the composite image data (e.g., stitch only face image data, remove background image data, etc.), and determine the total region and/or the total overlap region from the extracted portions. The region determiner 54 may also receive the composite image and/or extracted portions from a digital image editor, stitcher, etc., to determine the total region and/or the total overlap region.

The server apparatus 46 further includes a feature identifier 56 to identify the feature in the total region and/or in the total overlap region. For example, the feature identifier 56 may compare the entire total region and/or the entire total overlap region to characteristic facial data for one or more users (e.g., of the same or different gender, age, build, ethnicity, geographic location, etc.). The feature identifier 56 may also compare the entire total region and/or the entire total overlap region to user specific facial data (e.g., generated at boot up, pre-existing facial data, etc.).

The feature identifier 56 may also recognize facial objects within the total region and/or the total overlap region and compare the objects against characteristic feature data and/or the user specific feature data to identify the feature. The feature identifier 56 may further determine that the image data in the total region and/or in the total overlap region is the feature to be used for mental state evaluation when, for example, the total overlap region is scaled to the feature. In addition, the feature identifier 56 may identify the feature based on the position of the feature on the face. Thus, the feature identifier 56 may identify an area on the face that is to be evaluated, a landmark feature on the face that is to be evaluated, a partial or whole feature on the face that is to be evaluated, and so on.

The server apparatus 46 further includes a state determiner 58 to determine a mental state of the user such as, for example, an emotional state, a cognitive state, and/or a mental response unconsciously triggered by the nervous system. The state determiner 58 may retrieve (e.g., from an on-platform repository, via a communications interface, etc.) characteristic mental state data, user specific mental state data, etc., to determine the mental state. In this regard, only a portion of the characteristic mental state data and/or the user specific mental state data corresponding to the total region and/or the total overlap region may be retrieved.

The characteristic mental state data may include facial data associated with one or more states for one or more users (e.g., of the same or different gender, age, build, ethnicity, geographic location, etc.). The characteristic mental state data may include, for example, images of the users in particular emotional states, data for changes of a feature of the users between emotional states (e.g., feature appearance, feature disappearance, feature position changes, etc.), position of a feature of the users in particular emotional states (e.g., position of jowl of users in the state, etc.), etc. In addition, the user specific mental state data may include facial data associated with a user under observation. For example, the user specific mental state data may include images of the user in particular emotional states, differential data for changes of a feature of the user between emotional states (e.g., feature appearance, feature disappearance, feature position changes, etc.), position of a feature of the user in particular emotional states (e.g., position of jowl for the user in the state, etc.), etc.

In the illustrated example, the state determiner 58 includes a state evaluator 60 to evaluate the feature, in the total region and/or the total overlap region, based on the characteristic mental state data and/or the user specific mental state data. For example, the state evaluator 60 may determine a degree of match between the image data and the reference mental state data. In one example, sufficient confidence of a mental state determination may be achieved when a match threshold is satisfied (e.g., an approximate percent match between the feature and the reference mental state data). In this regard, confidence of the mental state determination may increase by defining an amount of overlap of the field of views of the image capture devices 38. In addition, confidence of the mental state determination may further increase by utilizing multiple perspectives from multiple image capture devices 38.

Confidence of the mental state determination may further increase by utilizing the sensor data of the user under observation. For example, the image data may provide a certain confidence level of a mental state (e.g., an approximate 95% likelihood that the user is happy based on a current position of a cheekbone and a jowl, etc.), which may increase when the state evaluator 60 also considers physiological data of the user (e.g., an approximate 99% likelihood that that user is happy based on the image data and decreased heart rate). The server apparatus 46 may also include other components such as, for example, a communications interface to communicate data, a processor to process data, a repository to store data, a power supply to provide power to one or more components of the server apparatus 46, etc. For example, the server apparatus 46 may provide the determined mental state to the client apparatus 62 via respective communication interfaces.

The illustrated client apparatus 62 may include a computing platform such as, for example, a desktop computer, a notebook computer, a tablet computer, a convertible tablet, a personal digital assistant (PDA), a mobile Internet device (MID), a media player, a smart phone, a smart televisions (TV), a radio, a wearable device (e.g., smart watch), a vehicle infotainment system, and so on. The client apparatus 62 may be a device of the user under observation. The client apparatus 62 may also be a device of an entity such as a rating entity, a social media entity, a news entity, an educational entity, an administrator, a third-party reseller, and so on.

In the illustrated example, the client apparatus 62 includes a user interface 64 which may include, for example, a graphical user interface, an auditory user interface, a tactile user interface, a command line interface, and so on. The user interface 64 may provide a representation of the mental state of the user being observed (e.g., a graphical representation, a textual representation, a sound, a pulse, etc.) based on the determined mental state. In addition, the user interface 64 may allow the user under observation and/or the observing user to configure a setting of the system 34, such as image capture settings, region determination settings, state evaluation settings, mental state data sharing settings, mental state representation settings, and so on. The client apparatus 62 may also include other components such as, for example, a communications interface to communicate data, a processor to process data, a repository to store data, a power supply to provide power to one or more components of the client apparatus 62, and so on.

While examples have shown separate components for illustration purposes, it is should be understood that one or more of the components of the system 34 may reside in the same and/or different physical and/or virtual locations, may be combined, omitted, bypassed, re-arranged, and/or be utilized in any order.

Figure 3:
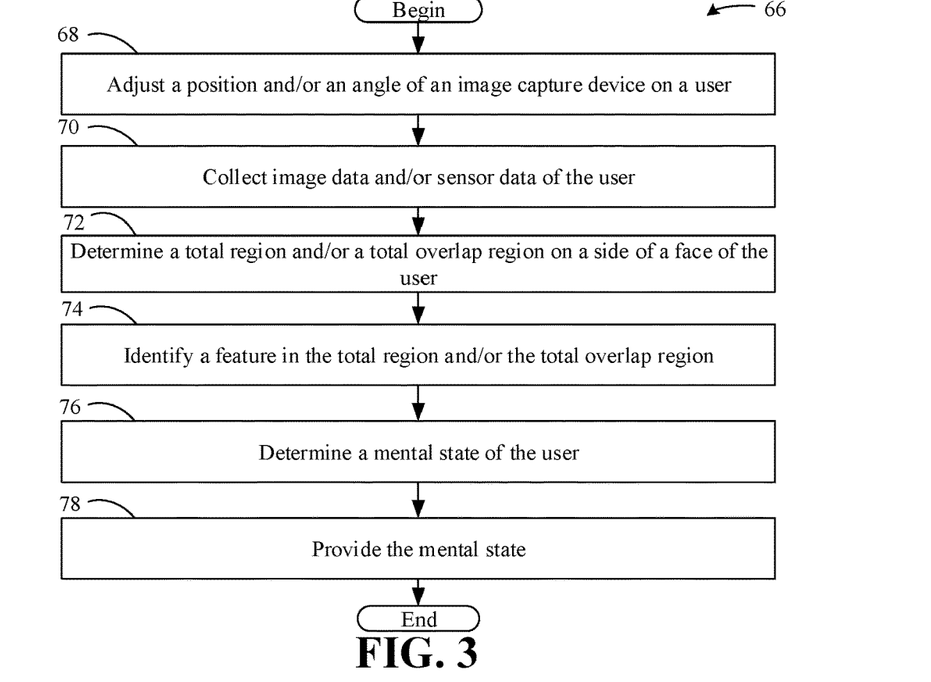
FIG. 3 is a flowchart of an example of a method to determine a mental state according to an embodiment.

Turning now to FIG. 3, an example of a method 66 to determine a mental state is shown according to an embodiment. The method 66 may be implemented as one or more modules in a set of logic instructions stored in a machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality hardware logic using circuit technology such as, for example, application specific integrated circuit (ASIC), complementary metal oxide semiconductor (CMOS) or transistor-transistor logic (TTL) technology, or any combination thereof. For example, computer program code to carry out operations shown in the method 66 may be written in any combination of one or more programming languages, including an object oriented programming language such as C++ or the like and conventional procedural programming languages, such as the "C" programming language or similar programming languages.

Illustrated processing block 68 adjusts a position and/or an angle of an image capture device for a user wearing the image capture device. The image capture device may include, for example, a video camera, a still camera, a thermal camera, and so on. Thus, block 68 may adjust a position and/or an angle of a camera via an actuator. Block 68 may also assist the user in adjusting the position and/or the angle of the image capture device. For example, block 68 may provide auditory guidance (e.g., via an output to a speaker, etc.), visual guidance (e.g., via an output to a display, etc.) to assist the user to position the image capture device.

Block 68 may calibrate the position and/or the angle of the image capture device for the user (e.g., user specific calibration, etc.). The calibration may occur at boot up, at power state change (e.g., when exiting hibernation, standby, etc.), and so on. Block 68 may also adjust the potions and/or the angle of the image capture device to set or change a total region and/or a total overlap region based on, for example, a perspective preference, a region preference, a feature preference, an accuracy preference, an efficiency preference, and so on.

Illustrated processing block 70 collects data of the user (e.g., the wearer of the image capture device and/or sensor, the user under observation, etc.). Block 70 may, for example, collect physiological data of the user from a physiological sensor (e.g., multiple sensors, etc.). The physiological sensor may include, for example, an EEG sensor, an ECG sensor, and EMG sensor, a PPG sensor, and so on. Block 70 may also collect image data for a side of a face of a user from the image capture device on the user.

The image data may include two or more perspectives of a feature (e.g., an area, a landmark feature, a partial feature, a whole feature, etc.) on the side of the face of the user. In one example, block 70 may collect image data including a plurality of features on the side of face of the user from the image capture device on the user. In another example, block 70 may collect image data for a different side of the face of the user from a different image capture device on the user. In this regard, the image data for the different side of the face of the user may include two or more perspectives of a feature on the different side of the face of the user.

Accordingly, for example, a field of view of an image capture device on the user at a first angle relative to the face may provide a first perspective, and the field of view of the image capture device on the user at a second angle relative to the face may provide a second perspective. In this case, the image capture device may pan across the face of the user to provide the first perspective and the second perspective (e.g., a series of perspective as the image capture device pans, etc.).

In addition, a field of view of a first image capture device on the user at a first angle relative to the face may provide a first perspective, and a field of view of a second image capture device on the user at a second angle relative to the face may provide a second perspective. In this case, two or more image capture devices may move to corresponding positions on the face to provide the first perspective and the second perspective, and concurrently capture image data when at rest.

Illustrated processing block 72 determines a total region and/or a total overlap region on a side of the face of the user. For example, the image data from one or more image capture devices may be combined to determine the total region and/or the total overlap region. In one example, a field of view may remain the same for an image capture device that pans, but perspectives change as the image capture device pans since the position of the field of view changes. In another example, multiple fields of view from multiple image capture devices provide multiple perspectives.

Block 72 may combine the image data including multiple perspectives to generate composite image data to determine the total region and/or the total overlap region. Block 72 may also extract portions of the image data including multiple perspectives to determine the total region and/or the total overlap region. Block 72 may, for example, determine the perimeter of the total region based on the boundary between a field of view and the face of the user. In addition, block 72 may determine the perimeter of the total overlap region based on the area of overlap of the multiple fields of views (and/or of multiple positions of the same field of view).

Illustrated processing block 74 identifies the feature in the total region and/or the total overlap region. Block 74 may compare an entire total region and/or an entire total overlap region to characteristic facial data for one or more users, to user specific facial data for the user under observation, etc. Block 74 may also recognize facial objects within the total region and/or the total overlap region, and compare the objects against the characteristic facial data and/or the user specific facial data. In addition, block 74 may determine that image data in the total region and/or in the total overlap region is the feature to be used for mental state evaluation. Moreover, block 70 may identify the feature based on a position of the feature on the face.

Illustrated processing block 76 determines the mental state of the user under observation based on the image data.

Block 76 may evaluate the feature (e.g., the identified feature, etc.) in the total region and/or the total overlap region based on characteristic mental state data to determine the mental state of the user. In addition, block 76 may evaluate the feature (e.g., the identified feature, etc.) in the total region and/or the total overlap region based on user specific mental state data to determine the mental state of the user. Additionally, block 76 may evaluate the image data with the sensor data to relatively increase reliability, accuracy, and so on.

Illustrated processing block 78 provides the mental state (e.g., determined mental state, calculated mental state, inferred mental state, etc.). Block 78 may, for example, provide the mental state to a state repository such as memory, storage, and so on. Block 78 may also provide the mental state to a function, such as an operating system, an application programming interface, an application, a program, and so on. In addition, block 78 may provide the mental state to an entity such as, for example, a rating entity, an academic entity, a social network, and so on.

In one example, the mental state may be provided to an Internet of Things (IoT) device to automatically modify fixed functionality of the IoT device according to the mental state of the user (e.g., dim lights when the user is in pain, lower room temperature when the user has a fever, begin making coffee when the user is drowsy or unfocused, etc.). In another example, the mental state may be provided to an educational entity. In the education domain, it may be important to understand the mental state of one or more students to allow a professor to better monitor the students and promote their academic or social growth. It may be important to monitor a student's interaction with peers to gain insight into social skills and to develop strategies to improve the interactions. Monitoring may occur unobtrusively (e.g., outside of the line of sight), inside or outside of the classroom.

An ability to determine mental states may provide real-time feedback on true mental dynamics of students, which may help a professor to deliver learning materials and motivate students to become engaged. In addition, a professor may receive feedback on a level of stress among students and have an opportunity to reverse the negative valence to help the students. In this regard, the professor may be able to review the effectiveness of attempted techniques to help the students.

In a further example, the mental state may be provided to a health entity. In the health domain, monitoring a patient's mental state may be interest to medical professionals in charge of the care of the patient. Insight of dynamics of a patient's mental state throughout the day may provide personalized medical care (e.g., psychological assistance, medication regimen, etc.). An ability to track patient mental state seamlessly and allow medical professionals to respond to actual needs may prolong the life span of the patient, improve the quality of life of the patient, etc.

In yet another example, mental state data may be provided to entities interested in customer service (e.g., museums, amusement parks, airports, banks, hospitals, etc.). In this regard, understanding customer experience based on mental states may provide valuable feedback for improving customer satisfaction. In the museum domain, a curator at a museum may wish to receive insight regarding the overall emotional impact that an art exhibition has on visitors or objectively access how well the displayed work is received by the public. In this regard, reactions such as disgust, surprise, fear, happiness, etc., may be captured while patrons are browsing leisurely, and provides a reliable success rating for the curators, artists, etc. Further non-limiting examples of entities may include marketing entities, advertisement entities, fashion entities, and so on.

While independent blocks and/or a particular order has been shown for illustration purposes, it should be understood that one or more of the blocks of any of the method 62 may be combined, omitted, bypassed, re-arranged, and/or flow in any order.

Figure 4:
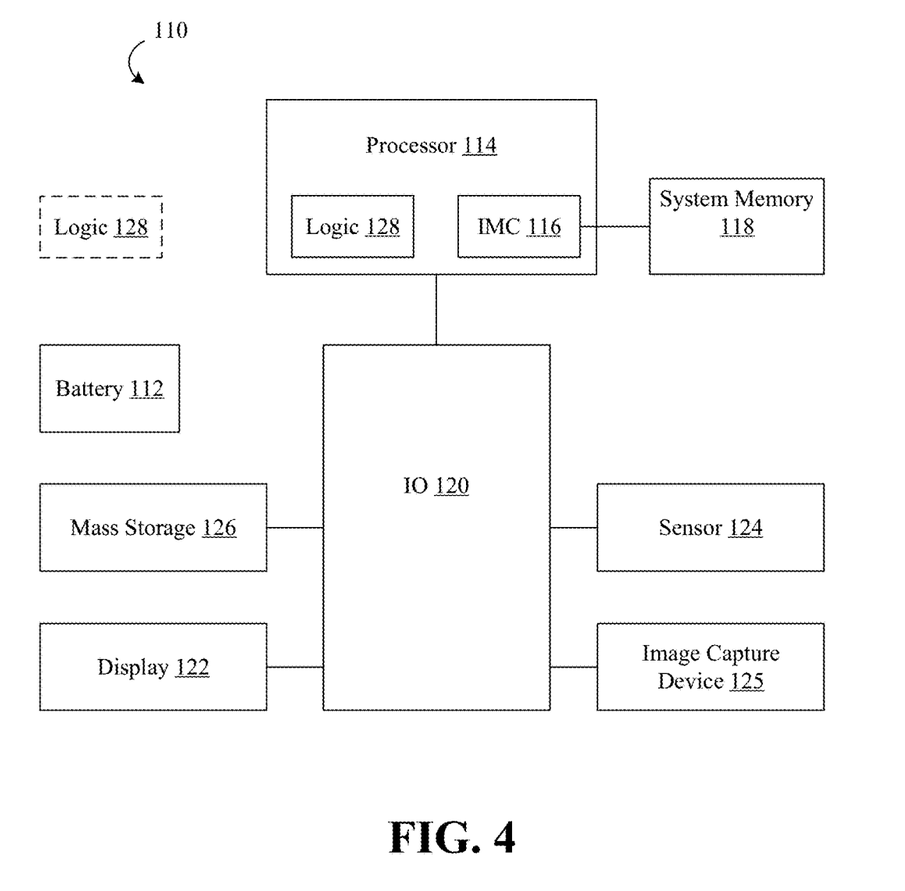
FIG. 4 is a block diagram of an example of a computing device according to an embodiment.

FIG. 4 shows a computing device 110 according to an embodiment. The computing device 110 may be part of a platform having computing functionality (e.g., personal digital assistant/PDA, notebook computer, tablet computer), communications functionality (e.g., wireless smart phone), imaging functionality, media playing functionality (e.g., smart television/TV), wearable functionality (e.g., watch, eyewear, headwear, footwear, jewelry) or any combination thereof (e.g., mobile Internet device/MID). In the illustrated example, the device 110 includes a battery 112 to supply power to the device 110 and a processor 114 having an integrated memory controller (IMC) 118, which may communicate with system memory 118. The system memory 118 may include, for example, dynamic random access memory (DRAM) configured as one or more memory modules such as, for example, dual inline memory modules (DIMMs), small outline DIMMs (SODIMMs), etc.

The illustrated device 110 also includes a input output (IO) module 118, sometimes referred to as a Southbridge of a chipset, that functions as a host device and may communicate with, for example, a display 122 (e.g., touch screen, liquid crystal display/LCD, light emitting diode/LED display), a sensor 124 (e.g., touch sensor, accelerometer, GPS, biosensor, etc.), an image capture device 125 (e.g., a camera, etc.), and mass storage 126 (e.g., hard disk drive/HDD, optical disk, flash memory, etc.). The processor 114 and the IO module 118 may be implemented together on the same semiconductor die as a system on chip (SoC).

The illustrated processor 114 may execute logic 128 (e.g., logic instructions, configurable logic, fixed-functionality logic hardware, etc., or any combination thereof) configured to implement any of the herein mentioned processes and/or control assistance technologies, including one or more components of the apparatus 10 (FIG. 1), one or more components of the system 34 (FIG. 2), and/or one or more blocks of the method 62 (FIG. 3), discussed above. In addition, one or more aspects of the logic 128 may alternatively be implemented external to the processor 114.

Additional Notes and Examples:

Example 1 may a system to determine a mental state comprising a wearable device including one or more image capture devices that are to be moveably coupled to a user to capture image data for a side of a face of the user, wherein the image data is to include two or more perspectives of a feature on the side of the face of the user, and a state determiner to determine a mental state of the user based on the image data.

Example 2 may include the system of Example 1, wherein the image capture device is to include one or more of, at least one image capture device moveably coupled with the user to pan across the side of the face of the user to capture the image data when the at least one image capture device is to pan, or at least two image capture devices moveably coupled with the user to be positioned to concurrently capture the image data when the at least two image capture devices are to be at rest.

Example 3 may include the system of any one of Example 1 to Example 2, further including a collector to collect the image data, a region determiner to determine a region on the side of the face of the user, wherein the region is to be based on two or more fields of view, a feature identifier to identify the feature in the region, an evaluator to one or more of evaluate the feature in the region based on characteristic mental state data to determine the mental state of the user or evaluate the feature in the region based on user specific mental state date to determine the mental state of the user, and an adjuster to one or more of calibrate an angle of at least one image capture device of the one or more image capture devices for the user or adjust the region based on one or more of a perspective preference, a region preference, a feature preference, an accuracy preference, or an efficiency preference.

Example 4 may include the system of any one of Example 1 to Example 3, further including a physiological sensor to provide physiological data of the user, a state evaluator to evaluate the feature and the physiological data to determine the mental state of the user, and an interface to provide the mental state of the user to one or more of a state repository, a function, or an entity.

Example 5 may include the apparatus to determine a mental state comprising a data collector to collect image data for a side of a face of a user from an image capture device on the user, wherein the image data is to include two or more perspectives of a feature on the side of the face of the user, and a state determiner to determine a mental state of the user based on the image data.

Example 6 may include the apparatus Example 5, wherein the data collector is to one or more of, collect image data including a plurality of features on the side of face of the user from the image capture device on the user, or collect image data for a different side of the face of the user from a different image capture device on the user, wherein the image data for the different side of the face of the user is to include two or more perspectives of a feature on the different side of the face of the user.

Example 7 may include the apparatus of any one of Example 5 to Example 6, wherein the feature is to include a partial feature on the side of the face of the user, and wherein the image data is to include two or more perspectives of the partial feature.

Example 8 may include the apparatus of any one of Example 5 to Example 7, wherein a field of view of the image capture device on the user at a first angle relative to the face is to provide a first perspective, and wherein the field of view of the image capture device on the user at a second angle relative to the face is to provide a second perspective.

Example 9 may include the apparatus of any one of Example 5 to Example 8, wherein a field of view of a first image capture device on the user at a first angle relative to the face is to provide a first perspective, and wherein a field of view of a second image capture device on the user at a second angle relative to the face is to provide a second perspective.

Example 10 may include the apparatus of any one of Example 5 to Example 9, further including a region determiner to determine a total region on the side of the face of the user, wherein the total region is to be based on the two or more fields of view, a feature identifier to identify the feature in the total region, and a state evaluator to one or more of evaluate the feature in the total region based on characteristic mental state data to determine the mental state of the user or evaluate the feature in the total region based on user specific mental state data to determine the mental state of the user.

Example 11 may include the apparatus of any one of Example 5 to Example 10, wherein the region determiner is to determine a total overlap region on the side of the face of the user, wherein the feature identifier is to identify the feature in the total overlap region, and wherein the state evaluator is to evaluate the feature in the total overlap region.

Example 12 may include the apparatus of any one of Example 5 to Example 11, further including an adjuster to one or more of calibrate an angle of the image capture device for the user or adjust one or more of a total region or a total overlap region based on one or more of a perspective preference, a region preference, a feature preference, an accuracy preference, or an efficiency preference.

Example 13 may include the apparatus of any one of Example 5 to Example 12, further including a physiological data collector to collect physiological data of the user from a physiological sensor, a state evaluator to evaluate the feature and the physiological data to determine the mental state of the user based, and an interface to provide the mental state of the user to one or more of a state repository, a function, or an entity.

Example 14 may include at least one computer readable storage medium comprising a set of instructions, which when executed by a computer, cause the computer to collect image data for a side of a face of a user from an image capture device on the user, wherein the image data is to include two or more perspectives of a feature on the side of the face of the user, and determine a mental state of the user based on the image data.

Example 15 may include the at least one computer readable storage medium of Example 14, wherein the instructions, when executed, cause the computer to one or more of collect image data including a plurality of features on the side of face of the user from the image capture device on the user or collect image data for a different side of the face of the user from a different image capture device on the user, wherein the image data for the different side of the face of the user is to include two or more perspectives of a feature on the different side of the face of the user.

Example 16 may include the at least one computer readable storage medium of any one of Example 14 to Example 15, wherein the feature is to include a partial feature on the side of the face of the user, and wherein the image data is to include two or more perspectives of the partial feature.

Example 17 may include the at least one computer readable storage medium of any one of Example 14 to Example 16, wherein a field of view of the image capture device on the user at a first angle relative to the face is to provide a first perspective, and wherein the field of view of the image capture device on the user at a second angle relative to the face is to provide a second perspective.

Example 18 may include the at least one computer readable storage medium of any one of Example 14 to Example 17, wherein a field of view of a first image capture device on the user at a first angle relative to the face is to provide a first perspective, and wherein a field of view of a second image capture device on the user at a second angle relative to the face is to provide a second perspective.

Example 19 may include the at least one computer readable storage medium of any one of Example 14 to Example 18, wherein the instructions, when executed, cause the computer to determine a total region on the side of the face of the user, wherein the total region is to be based on the two or more fields of view, identify the feature in the total region, and one or more of evaluate the feature in the total region based on characteristic mental state data to determine the mental state of the user or evaluate the feature in the total region based on user specific mental state data to determine the mental state of the user.

Example 20 may include the at least one computer readable storage medium of any one of Example 14 to Example 19, wherein the instructions, when executed, cause the computer to determine a total overlap region on the side of the face of the user, identify the feature in the total overlap region, and evaluate the feature in the total overlap region.

Example 21 may include the at least one computer readable storage medium of any one of Example 14 to Example 20, wherein the instructions, when executed, cause the computer to one or more of calibrate an angle of the image capture device for the user or adjust one or more of a total region or a total overlap region based on one or more of a perspective preference, a region preference, a feature preference, an accuracy preference, or an efficiency preference.

Example 22 may include the at least one computer readable storage medium of any one of Example 14 to Example 21, wherein the instructions, when executed, cause the computer to collect physiological data of the user from a physiological sensor, evaluate the feature and the physiological data to determine the mental state of the user based, and provide the mental state of the user to one or more of a state repository, a function, or an entity.

Example 23 may include a method to determine a mental state comprising collecting image data for a side of a face of a user from an image capture device on the user, wherein the image data includes two or more perspectives of a feature on the side of the face of the user and determining a mental state of the user based on the image data.

Example 24 may include the method of Example 23, further including one or more of collecting image data including a plurality of features on the side of face of the user from the image capture device on the user or collecting image data for a different side of the face of the user from a different image capture device on the user, wherein the image data for the different side of the face of the user includes two or more perspectives of a feature on the different side of the face of the user.

Example 25 may include the method of any one of Example 23 to Example 24, wherein the feature includes a partial feature on the side of the face of the user, and wherein the image data includes two or more perspectives of the partial feature.

Example 26 may include the method of any one of Example 23 to Example 25, wherein a field of view of the image capture device on the user at a first angle relative to the face provides a first perspective, and wherein the field of view of the image capture device on the user at a second angle relative to the face provides a second perspective.

Example 27 may include the method of any one of Example 23 to Example 26, wherein a field of view of a first image capture device on the user at a first angle relative to the face provides a first perspective, and wherein a field of view of a second image capture device on the user at a second angle relative to the face provides a second perspective.

Example 28 may include the method of any one of Example 23 to Example 27, further including determining a total region on the side of the face of the user, wherein the total region is based on the two or more fields of view, identifying the feature in the total region, and one or more of evaluating the feature in the total region based on characteristic mental state data to determine the mental state of the user or evaluating the feature in the total region based on user specific mental state data to determine the mental state of the user.

Example 29 may include the method of any one of Example 23 to Example 28, further including determining a total overlap region on the side of the face of the user, identifying the feature in the total overlap region, and evaluating the feature in the total overlap region.

Example 30 may include the method of any one of Example 23 to Example 29, further including one or more of calibrating an angle of the image capture device for the user or adjusting one or more of a total region or a total overlap region based on one or more of a perspective preference, a region preference, a feature preference, an accuracy preference, or an efficiency preference.

Example 31 may include the method of any one of Example 23 to Example 30, further including collecting physiological data of the user from a physiological sensor, evaluating the feature and the physiological data to determine the mental state of the user based, and providing the mental state of the user to one or more of a state repository, a function, or an entity.

Example 32 may include an apparatus to determine a mental state comprising means for collecting image data for a side of a face of a user from an image capture device on the user, wherein the image data includes two or more perspectives of a feature on the side of the face of the user, and means for determining a mental state of the user based on the image data.

Example 33 may include the apparatus of Example 32, further including one or more of means for collecting image data including a plurality of features on the side of face of the user from the image capture device on the user or means for collecting image data for a different side of the face of the user from a different image capture device on the user, wherein the image data for the different side of the face of the user includes two or more perspectives of a feature on the different side of the face of the user.

Example 34 may include the apparatus of any one of Example 32 to Example 33, wherein the feature includes a partial feature on the side of the face of the user, and wherein the image data includes two or more perspectives of the partial feature.

Example 35 may include the apparatus of any one of Example 32 to Example 34, wherein a field of view of the image capture device on the user at a first angle relative to the face provides a first perspective, and wherein the field of view of the image capture device on the user at a second angle relative to the face provides a second perspective.

Example 36 may include the apparatus of any one of Example 32 to Example 35, wherein a field of view of a first image capture device on the user at a first angle relative to the face provides a first perspective, and wherein a field of view of a second image capture device on the user at a second angle relative to the face provides a second perspective.

Example 37 may include the apparatus of any one of Example 32 to Example 36, further including means for determining a total region on the side of the face of the user, wherein the total region is to be based on the two or more fields of view, means for identifying the feature in the total region, and one or more of means for evaluating the feature in the total region based on characteristic mental state data to determine the mental state of the user or means for evaluating the feature in the total region based on user specific mental state data to determine the mental state of the user.

Example 38 may include the apparatus of any one of Example 32 to Example 37, further including means for determining a total overlap region on the side of the face of the user, means for identifying the feature in the total overlap region, and means for evaluating the feature in the total overlap region.

Example 39 may include the apparatus of any one of Example 32 to Example 38, further including one or more of means for calibrating an angle of the image capture device for the user or means for adjusting one or more of a total region or a total overlap region based on one or more of a perspective preference, a region preference, a feature preference, an accuracy preference, or an efficiency preference.

Example 40 may include the apparatus of any one of Example 32 to Example 39, further including means for collecting physiological data of the user from a physiological sensor, means for evaluating the feature and the physiological data to determine the mental state of the user based, and means for providing the mental state of the user to one or more of a state repository, a function, or an entity.

Thus, techniques described herein may provide freedom of movement to capture correct mental states of a user without feelings of pressure or nervousness associated with being observed by a person (or a device in the line of sight) while performing a task. In addition, techniques may provide a battery operated, head-worn wearable device with one or more cameras and/or sensors. Moreover, unconventional forward facing camera angles may capture partial facial regions to assist in emotion recognition. In this regard, camera angles may be chosen that are not physically possible for a human. In one example, six cameras (e.g., three on opposite sides of a face) may be utilized. In addition, the cameras may capture image data simultaneously from different angles to provided relatively improved accuracy.

Embodiments may also scale an amount of overlap in field of views captures by multiple cameras. When all the field of views of the cameras are combined, a relatively larger facial area may be captured. In addition, a total overlap region captured by the multiple cameras simultaneously may provide multiple data from independent sources to increase accuracy and/or reliability of predictions derived from that area of the face. Moreover, the total region and/or the total overlap region may be moved or resized to accommodate preferences (e.g., efficiency preferences). In addition, calibration may be user specific, may maximize the effectiveness of the total region and/or the overlap regions, and/or may minimize a need for separate registration of captured images.

Also, sensors such as EMG and/or PPG sensors may be placed on areas that have muscle mass, vasculature, etc. (e.g., face, neck, etc.) to increase accuracy and/or reliability of predictions derived from that area of the face. Physiological sensors may detect involuntary muscle movements, heart rate, blood oxygen saturations, breathing rates, and so on. In this regard, metrics from the physiological sensors may supplement, elucidate, and or corroborate mental state determinations from image data. For example, the image data and the sensor data may provide mental state information such as nervousness, happiness, sadness, stress, and so on. In one example, the sensors may be positioned on the head as well as in close proximity to the cameras to maximize comfort and convenience for the wearer.

Embodiments are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/ or single-ended lines.

Example sizes/models/values/ranges may have been given, although embodiments are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments, it should be apparent to one skilled in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

As used in this application and in the claims, a list of items joined by the term "one or more of" or "at least one of" may mean any combination of the listed terms. For example, the phrases "one or more of A, B or C" may mean A; B; C; A and B; A and C; B and C; or A, B and C. In addition, a list of items joined by the term "and so forth" or "etc." may mean any combination of the listed terms as well any combination with other terms.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

We claim:

1. A system to determine a mental state comprising:
a wearable device including one or more image capture devices that are to be moveably coupled to a user and that have corresponding fields of view orientated in a direction from a rearward facial portion of a same side of a face of the user towards a field of view of the user to capture image data for the side of the face of the user, wherein the one or more image capture devices include one or more of at least one image capture device to pan vertically across the side of the face of the user to capture the image data or at least two image capture devices that are vertically spaced apart to concurrently capture the image data for the side of the face of the user, and wherein the image data is to include two or more perspectives from different angles of a feature on the side of the face of the user, a region determiner logic circuit to determine a total overlap region on the side of the face of the user, a feature identifier logic circuit to identify the feature in the total overlap region, a state determiner logic circuit to determine a mental state of the user based on each of the two or more perspectives from the different angles of the feature in the total overlap region, and a communication interface to transmit mental state data corresponding to the mental state of the user to one or more of a data storage device and a client apparatus.

2. The system of claim 1, wherein one or more of the at least one image capture device is to capture the image data when the at least one image capture device is to pan or the at least two image capture devices are to concurrently capture the image data when the at least two image capture devices are to be at rest.

3. The system of claim 1, further including, a collector logic circuit to collect the image data, the region determiner logic circuit to determine a total region on the side of the face of the user, wherein the total region is to be based on two or more fields of view of the corresponding fields of view, and wherein the total overlap region is to be located in the total region, an evaluator logic circuit to one or more of, evaluate the feature in the total overlap region based on characteristic mental state data to determine the mental state of the user, or evaluate the feature in the total overlap region based on user specific mental state data to determine the mental state of the user, and an adjuster logic circuit to one or more of, calibrate an angle of an image capture device of the one or more image capture devices for the user, or adjust one or more of the total region or the total overlap region based on one or more of a perspective preference, a region preference, a feature preference, an accuracy preference, or an efficiency preference.

4. The system of claim 1, further including, a physiological sensor to provide physiological data of the user, and a state evaluator logic circuit to evaluate the feature and the physiological data to determine the mental state of the user.

5. An apparatus to determine a mental state comprising:

a communication interface to receive image data for a same side of a face of a user from one or more image capture devices that are to be moveably coupled to the user and that have corresponding fields of view orientated in a direction from a rearward facial portion of the side of the face of the user towards a field of view of the user to capture image data for the side of the face of a user, wherein the one or more image capture devices include one or more of at least one image capture device to pan vertically across the side of the face of the user to capture the image data or at least two image capture devices that are vertically spaced apart to concurrently capture the image data for the side of the face of the user, and wherein the image data is to include two or more perspectives from different angles of a feature on the side of the face of the user, a region determiner logic circuit to determine a total overlap region on the side of the face of the user, a feature identifier logic circuit to identify the feature in the total overlap region, and a state determiner logic circuit to determine a mental state of the user based on each of the two or more perspectives from the different angles of the feature in the total overlap region.

6. The apparatus of claim 5, further including a data collector logic circuit to, collect image data including a plurality of features on the side of face of the user from the one or more image capture devices on the user, and collect image data for a different side of the face of the user from an image capture device on the user having a field of view orientated in a direction from a rearward facial portion of the different the side of the face of the user towards the field of view of the user to capture the image data for the different side of the face of the user, wherein the image data for the different side of the face of the user is to include two or more perspectives from different angles of a feature on the different side of the face of the user.

7. The apparatus of claim 5, wherein the feature is to include a partial feature on the side of the face of the user, and wherein the image data is to include two or more perspectives of the partial feature.

8. The apparatus of claim 5, wherein a field of view of the at least one image capture device on the user at a first angle relative to the side of the face is to provide a first perspective of the two or more perspectives, and wherein the field of view of the at least one image capture device on the user at a second angle relative to the side of the face is to provide a second perspective of the two or more perspectives.

9. The apparatus of claim 5, wherein a field of view of a first image capture device of the at least two image capture devices on the user at a first angle relative to the face is to provide a first perspective of the two or more perspectives, and wherein a field of view of a second image capture device of the at least two image capture devices on the user at a second angle relative to the face is to provide a second perspective of the two or more perspectives.

10. The apparatus of claim 5, further including, the region determiner logic circuit to determine a total region on the side of the face of the user, wherein the total region is to be based on the two or more fields of view of the corresponding fields of view, and wherein the total overlap region is to be located in the total region, and a state evaluator logic circuit to, evaluate the feature in the total overlap region based on characteristic mental state data to determine the mental state of the user, and evaluate the feature in the total overlap region based on user specific mental state data to determine the mental state of the user.

11. The apparatus of claim 5, further including an adjuster logic circuit to, calibrate an angle of an image capture device of the one or more image capture devices for the user, and adjust one or more of a total region or the total overlap region based on one or more of a perspective preference, a region preference, a feature preference, an accuracy preference, or an efficiency preference.

12. The apparatus of claim 5, further including,
a physiological data collector logic circuit to collect physiological data of the user from a physiological sensor, and
a state evaluator logic circuit to evaluate the feature and the physiological data to determine the mental state of the user based, wherein the apparatus is to transmit mental state data corresponding to the mental state of the user to one or more of a data storage device or a client apparatus.

13. At least one non-transitory computer readable storage medium comprising a set of instructions, which when executed by a computer, cause the computer to:
receive image data for a same side of a face of a user from one or more image capture devices that are to be moveably coupled to the user and that have corresponding fields of view orientated in a direction from a rearward facial portion of the side of the face of the user towards a field of view of the user to capture image data for the side of the face of a user, wherein the one or more image capture devices include one or more of at least one image capture device to pan vertically across the side of the face of the user to capture the image data or at least two image capture devices that are vertically spaced apart to concurrently capture the image data for the side of the face of the user, and wherein the image data is to include two or more perspectives from different angles of a feature on the side of the face of the user;
determine a total overlap region on the side of the face of the user;
identify the feature in the total overlap region; and
determine a mental state of the user based on each of the two or more perspectives from the different angles of the feature in the total overlap region.

14. The at least one non-transitory computer readable storage medium of claim 13, wherein the instructions, when executed, cause the computer to one or more of:
collect image data including a plurality of features on the side of face of the user from the one or more image capture devices on the user; or
collect image data for a different side of the face of the user from an image capture device on the user having a field of view orientated in a direction from a rearward facial portion of the different the side of the face of the user towards the field of view of the user to capture the image data for the different side of the face of the user, wherein the image data for the different side of the face of the user is to include two or more perspectives from different angles of a feature on the different side of the face of the user.

15. The at least one non-transitory computer readable storage medium of claim 13, wherein the instructions, when executed, cause the computer to:
determine a total region on the side of the face of the user, wherein the total region is to be based on the two or more fields of view of the corresponding fields of view, and wherein the total overlap region is to be located in the total region;
and
one or more of:
evaluate the feature in the total overlap region based on characteristic mental state data to determine the mental state of the user; or
evaluate the feature in the total overlap region based on user specific mental state data to determine the mental state of the user.

16. The at least one non-transitory computer readable storage medium of claim 13, wherein the instructions, when executed, cause the computer to one or more of:
calibrate an angle of an image capture device of the one or more image capture devices for the user; or
adjust one or more of a total region or the total overlap region based on one or more of a perspective preference, a region preference, a feature preference, an accuracy preference, or an efficiency preference.

17. The at least one non-transitory computer readable storage medium of claim 13, wherein the instructions, when executed, cause the computer to:
collect physiological data of the user from a physiological sensor;
evaluate the feature and the physiological data to determine the mental state of the user based; and
transmit mental state data corresponding to the mental state of the user to one or more of a data storage device or a client apparatus.

18. A method to determine a mental state comprising:
receiving image data for a same side of a face of a user from one or more image capture devices that are moveably coupled to the user and that have corresponding fields of view orientated in a direction from a rearward facial portion of the side of the face of the user towards a field of view of the user to capture image data for the side of the face of a user, wherein the one or more image capture devices include one or more of at least one image capture device to pan vertically across the side of the face of the user to capture the image data or at least two image capture devices that are vertically spaced apart to concurrently capture the image data for the side of the face of the user, and wherein the image data includes two or more perspectives from different angles of a feature on the side of the face of the user;
determining a total overlap region on the side of the face of the user;
identifying the feature in the total overlap region; and
determining a mental state of the user based on each of the two or more perspectives from the different angles of the feature in the total overlap region.

19. The method of claim 18, further including one or more of:
collecting image data including a plurality of features on the side of face of the user from the one or more image capture devices on the user; or
collecting image data for a different side of the face of the user from an image capture device on the user having a field of view orientated in a direction from a rearward facial portion of the different the side of the face of the user towards the field of view of the user to capture the image data for the different side of the face of the user, wherein the image data for the different side of the face of the user includes two or more perspectives from different angles of a feature on the different side of the face of the user.

20. The method of claim 18, further including
determining a total region on the side of the face of the user, wherein the total region is based on the two or more fields of view of the corresponding fields of view, and wherein the total overlap region is located in the total region;

and
one or more of:
   evaluating the feature in the total overlap region based on characteristic mental state data to determine the mental state of the user; or
   evaluating the feature in the total overlap region based on user specific mental state data to determine the mental state of the user.

21. The method of claim 18, further including one or more of:
   calibrating an angle of an image capture device of the one or more image capture devices for the user; or
   adjusting one or more of a total region or the total overlap region based on one or more of a perspective preference, a region preference, a feature preference, an accuracy preference, or an efficiency preference.

22. The method of claim 18, further including:
   collecting physiological data of the user from a physiological sensor;
   evaluating the feature and the physiological data to determine the mental state of the user based; and
   transmitting mental state data corresponding to the mental state of the user to one or more of a data storage device or a client apparatus.

* * * * *